(12) United States Patent
Cuzzato et al.

(10) Patent No.: US 6,300,529 B1
(45) Date of Patent: *Oct. 9, 2001

(54) PROCESS FOR PREPARING HCFC-123

(75) Inventors: Paolo Cuzzato, Treviso; Francesco Rinaldi; Letanzio Bragante, both of Padova, all of (IT)

(73) Assignee: Ausimont S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,318

(22) Filed: May 26, 1998

(30) Foreign Application Priority Data

May 27, 1997 (IT) .............................. MI97A1237

(51) Int. Cl.[7] ..................................... C07C 19/08
(52) U.S. Cl. ............................................. 570/163
(58) Field of Search ............................... 570/163

(56) References Cited

U.S. PATENT DOCUMENTS

| 4,967,023 | 10/1990 | Carmello et al. . |
| 5,345,014 | 9/1994 | Cuzzato . |
| 5,367,103 | 11/1994 | Guglielmo et al. . |
| 5,414,167 | 5/1995 | Bragante et al. . |

FOREIGN PATENT DOCUMENTS

| 0 511 612 A3 | 4/1992 | (EP) . |
| 0 569 832 A1 | 11/1993 | (EP) . |
| 5-32567 | 2/1991 | (JP) . |
| 4-360844 | 6/1991 | (JP) . |
| WO 92/02476 | 2/1992 | (WO) . |

*Primary Examiner*—Alan Siegel
(74) *Attorney, Agent, or Firm*—Arent Fox Kintner Plotkin & Kahn, PLLC

(57) ABSTRACT

Process for preparing HCFC-123 with a content of olefins lower than 10 ppm and very small amounts of HCFC-123a and 123b by dismutation of HCFC-124 in gaseous phase by contact with a catalyst which essentially consists of three valence chromium oxide supported on aluminum fluoride, at temperatures in the range 150°–260° C., and with contact times between 5–25 sec.

6 Claims, No Drawings

PROCESS FOR PREPARING HCFC-123

The present invention relates to the synthesis of $CF_3$—$CHCl_2$ (HCFC-123) having a very low content of undesired unsaturated components.

More specifically the present invention relates to the use of a specific process for preparing HCFC-123 leading to the desired product with very low amounts of $CF_3$—$CF$=$CCl$—$CF_3$ (CFC-1317) and $CF_3$—$CH$=$CCl$—$CF_3$ (HCFC-1326), said process having a selectivity in useful products not lower than 98%.

HCFC-123 is an hydrochlorofluorocarbon (HCFC) having a low ODP (low impact on the ozone layer reduction) whose production is therefore of remarkable industrial interest, for intance as foaming agent for polymeric foams, as fire-extinguishing agent and as refrigerant in cooling plants, etc.

For these reasons the HCFC-123 purity requirements must be extremely high: in particular it is desirable that it has a content not higher than 10 ppm of unsaturated compounds (collectively indicated hereinafter by the name of "olefins"), as $CF_2$=$CCl_2$ (CFC-1112a), HCFC-1326 and HFC-1317. These olefinic compounds are indeed toxic and unstable. If the processes leading to the formation of HCFC-123 bring to an olefin content over the above limit, other phases leading to the reduction of said compounds must be used in the industrial plants.

It is important to note that the HCFC-123 separation from these olefins by fractional distillation is often extremely difficult, therefore it is almost impossible to obtain the above mentioned purity in industiral scale. Consequently, remarkable research efforts have been made to succeed in finding an effective method to purify HCFC-123 at industrial level.

For instance, it is possible to turn said olefins into quite harmless saturated products (and/or more easily separable). In JP 04/360,844, the catalytic hydrogenation of CFC-1317 contained in HCFC-123 by means of molecular hydrogen on a platinum catalyst is described.

In JP 05/32,567 the use of molecular chlorine on active carbon by chlorination of $CF_2$=$CCl_2$ (CFC-1112a) contained in the HCFC-123 is described, thus obtaining HCFC-123 with a residual content of olefins of 18 ppm.

In U.S. Pat. No. 5,367,103 the use of molecular fluorine to remove CFC-1112a from HCFC-123 is described.

Another method often described in the art is the selective adsorption of olefins by means of suitable adsorbers. For instance in EP 511,612 the HCFC-1326 is removed from HCFC-123 by adsorption on zeolite Y.

Therefore each process needs at least a supplementary step in the contaminated HCFC-123 treatment, sometimes neither sufficient to obtain the desired purity.

Moreover, the HCFC-123, commomly produced from perchloro ethylene and HF by a fluorination catalyst, see for instance U.S. Pat. No. 4,967,023, contains remarkable amounts of the so called "asymmetrical" isomers HCFC-123a and 123b, respectively $CF_2Cl$—$CFHCl$ and $CF_2H$—$CCl_2F$, undesired due to their poor stability, and therefore transformed into more easily separable compounds (see U.S. Pat. No. 5,414,167) or isomerized to the $CF_3$—$CH_2Cl$ (HCFC-133a) which is thermodynamically more stable. As it can be seen, also in this process at least a supplementary treatment of the product is required for the reduction of the undesired by products.

Therefore it is of remarkable industrial interest to have available a process having a high selectivity, not lower than 98%, to prepare HCFC-123 free as much as possible both from the olefins and from the asymmetric isomers, thus eliminating further additional purification treatments.

The Applicant has unexpectedly and surprisingly found that it is possible to obtain HCFC-123 containing very small amounts of olefins, lower than 10 ppm, if the process described hereinafter is used.

It is therefore an object of the present invention a process for preparing HCFC-123 having a content of olefins lower than 10 ppm by dismutation of gaseous $CHClF$—$CF_3$ (HCFC-124) by contact with a catalyst which essentially consists of three valence chromium oxide ($Cr_2O_3$) supported on aluminum fluoride, at temperatures comprised between 150° C. and 260° C., preferably 180° C. and 220° C. and with contact times between 5–25 sec, preferably 10–20 sec.

It has been found that the temperature is the most important reaction parameter, while the contact time has comparatively a lower effect.

The lower is the temperature in the indicated range, the better are the results in terms of global selectivity, while the conversion is obviously better at higher temperatures.

The HCFC-124 which is used as reactant in the dismutation is produced by perchloroethylene fluorination, therefore it has high production costs. It is therefore necessary that the disputation process has a selectivity to HCFC-123 and $CHF_2$—$CF_3$ (HFC-125) higher than or equal to 98% to be an industrially and economically acceptable process.

Moreover from the environmental point of view it is preferable to have high selectivity since the by-products are mainly formed by CFC of which the dangerous effect on the ozone layer is well known.

It is well known that the CFCs disposal requires suitable devoted incineration plants.

As aluminum fluoride, used as support, according to the present invention, it is meant the alumina fluorination product, having a fluorine content not lower than 90%, preferably not lower than 95%, of the stoichiometric. Preferably the granulometry of the support and of its precursor is suitable to be used in fluidized bed.

The preferred support is the 100% by weight $AlF_3$, preferably in the gamma and/or beta structure.

$AlF_3$ can also contain the delta structure, generally up to 30% by weight.

The Cr content in the supported catalyst generally ranges between 1 and 15% by weight, calculated as Cr in the catalyst.

As chromium oxide supported on $AlF_3$ it is meant trivalent Cr oxide $Cr_2O_3$; during the activation and the process of the invention, reaches the equilibrium with the reactants, by partial transformation into oxyfluoride, fluoride and oxychloride.

The catalyst of the invention is particularly suitable to be used in the fluidized bed plants.

The preferred general procedure for preparing the catalyst consists in impregnating a certain amount of the support with a concentrated solution of a soluble Cr(III) salt, for instance chloride. The volume of the impregnating solution is equal to or lower than the support pore volume, in order to avoid the adhesion among the granules of the same. In particular the catalyst is prepared according to Example 7 of U.S. Pat. No. 5,345,014, herein incorporated by reference.

The catalyst of the invention maintains an high activity during the time wherefore it does not require frequent regeneration processes. These are carried out according to the method described in U.S. Pat. No. 4,967,023, herein incorporated by reference.

The following examples are given for illustrative purposes but are not limitative of the scope of the present invention.

EXAMPLE 1A

Catalyst Preparation

A sample of aluminum fluoride having granulometry suitable for a fluidized bed is "dry" impregnated with a concentrated aqueous solution of $CrCl_3 \times 6H_2O$, in the range of 492 g of chromium chloride for 1000 g of aluminium fluoride. The so obtained catalyst is calcined at 400° C. under nitrogen flow (about 100 NL/h) for 10 hours, then fluorinated at 360° C. with anhydrous HF for 24 hours.

EXAMPLE 1B

Dismutation of HCFC-124

300 cc of the catalyst of Example 1A are introduced in a 50 mm tubular reactor, electrically heated and equipped with porous septum at the base. At the temperature of 240° C., 273 g/h (2 moles/h) of HCFC-124 are fed to the reactor, thus achieving a contact time equal to about 13 sec. The gases coming out from the reactor are washed in water to remove acidity traces and analyzed by gas chromatography GC with HWD detector (thermoconductibility). The following analysis is representative of the obtained results:

| | |
|---|---|
| HFC-125 | 39.8%mole |
| HCFC-124 | 25.5 |
| HCFC-123 | 33.4 |
| Others | 1.3 |

The HCFC-124 conversion is equal to 74.5% and the global selectivity of the process (CFC-125+HCFC-123) is of 98%. The amount of olefins (CFC-1112a+HCFC-1326+CFC-1317) in the reaction products is too small to be directly measured, wherefore the analysis is repeated by gas chromatograpohy/GC-MS mass. The following results are obtained:

| | |
|---|---|
| CFC-1112a | 0.16 ppm |
| HCFC-1326 | <0.1 ppm |
| CFC-1317 | <0.1 ppm |

EXAMPLE 1C

The HCFC-124 disputation of Example 1B is repeated in different temperature conditions and contact times: the relative results are summarized in Table 1.

It can be noted how there is never a measurable amount of olefins up to the temperature of 280° C., however at 280° C. the selectivity is lower than 98%.

EXAMPLE 2

Example 1B is repeated at 320° C. with a HCFC-124 feeding of 1.3 mole/hour, thus achieving a contact time of about 17 sec. The results are reported in the last column of Table 1. As it can be seen, the HCFC-124 conversion increases as well as the olefins content, while the global selectivity of the process decreases.

TABLE 1

| Examples | 1C | 1C | 1B | 1C | 1C comp | 1C comp | 1C comp | 2 comp |
|---|---|---|---|---|---|---|---|---|
| Feed 124 mole/h | 2.0 | 2.0 | 2.0 | 2.0 | 2.0 | 2.0 | 2.0 | 1.3 |
| Temperature, ° C. | 180 | 220 | 240 | 260 | 280 | 300 | 320 | 320 |
| Contact time, sec. | 14.5 | 13.3 | 12.8 | 12.3 | 11.9 | 11.5 | 11.1 | 17.1 |
| 125 % mole | 22.36 | 27.01 | 39.80 | 45.00 | 50.64 | 50.19 | 51.91 | 53.75 |
| 124 | 56.50 | 47.20 | 25.53 | 21.77 | 18.56 | 19.12 | 18.14 | 15.80 |
| 133 | 0.03 | 0.06 | 0.16 | 0.31 | 0.65 | 1.06 | 2.22 | 2.81 |
| 114 | 0.02 | 0.07 | 0.10 | 0.16 | 0.23 | 0.44 | 0.69 | 1.05 |
| 123a + b | 0.01 | 0.02 | 0.02 | 0.08 | 0.03 | 0.03 | 0.03 | 0.00 |
| 123 | 21.06 | 25.47 | 33.36 | 31.39 | 27.90 | 26.24 | 22.00 | 20.11 |
| 1110 | 0.00 | 0.05 | 0.68 | 1.06 | 0.72 | 0.60 | 0.55 | 1.03 |
| Others | 0.02 | 0.11 | 0.35 | 0.23 | 1.27 | 2.31 | 4.47 | 5.45 |
| Conv. 124 | 43.50 | 52.80 | 74.47 | 78.23 | 81.44 | 80.88 | 81.86 | 84.20 |
| Sel. 123 + 125 | 1.00 | 0.99 | 0.98 | 0.98 | 0.96 | 0.95 | 0.90 | 0.88 |
| 123a + b/123 tot % | 0.05 | 0.07 | 0.06 | 0.25 | 0.10 | 0.12 | 0.12 | 0.02 |
| 1112a, ppm | n.d. | n.d. | 0.16 | <0.1 | <0.1 | n.d. | n.d. | n.d. |
| 1317, ppm | n.d. | <0.5 | <0.1 | <0.1 | <0.1 | <0.5 | 1 | 1.6 |
| 1326, ppm | n.d. | <0.5 | <0.1 | <0.1 | <0.1 | 4.2 | 9.5 | 11.4 |
| Olefines in 123 ppm | n.d. | <10 | <10 | <10 | <10 | 16 | 48 | 65 |

What is claimed is:

1. A method for reducing the olefin content of HCFC-123 to values lower than 10 ppm by using as process for preparing the HCFC-123 the dismutation process of gaseous HCFC-124 by contact with a catalyst which essentially consists of three valence chromium oxide ($CR_2O_3$) supported on aluminum fluoride, at temperatures comprised between 150° C. and 260° C., and with contact times between 5–25 seconds, wherein said dismutation process has a selectivity of useful products HCFC-123 and HCFC-125 of not less than 97.65% by moles.

2. The method according to claim 1 wherein the temperature is comprised between 180 and 220° C. and the contact times between 10–20 seconds.

3. The method according to claim 1, wherein the aluminum floride is an alumina florination product, with a flourine content not lower than 90% of the theoretical flourine content of pure $AlF_3$.

4. The method according to claim 1, wherein the support is 100% by weight $AlF_3$ in the gamma structure.

5. The method according to claim 1 wherein the chromium oxide contains oxyfluoride, fluoride and oxychloride.

6. The method according to claim 1 wherein the aluminum fluoride is an alumina fluorination product, with a fluorine content not lower than 95% of the theoretical fluorine content of pure $AlF_3$.

* * * * *